United States Patent
Hobart et al.

(10) Patent No.: US 6,575,964 B1
(45) Date of Patent: *Jun. 10, 2003

(54) SELECTIVE APERTURE FOR LASER DELIVERY SYSTEM FOR PROVIDING INCISION, TISSUE ABLATION AND COAGULATION

(75) Inventors: James L. Hobart, Los Altos, CA (US); Daniel K. Negus, Los Altos, CA (US); Ken Gott, Santa Clara, CA (US); Rene Hugues, Santa Clara, CA (US)

(73) Assignee: Sciton, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/498,937

(22) Filed: Feb. 4, 2000

Related U.S. Application Data (63) Continuation-in-part of application No. 09/018,104, filed on Feb. 3, 1998.
(60) Provisional application No. 60/118,635, filed on Feb. 4, 1999.

(51) Int. Cl.[7] .............................................. A61B 18/18
(52) U.S. Cl. ............................... 606/10; 606/3; 606/13; 607/89
(58) Field of Search .................. 606/2, 3–19; 607/88, 607/89; 372/9, 33, 92, 103, 104

(56) References Cited

U.S. PATENT DOCUMENTS

| | | |
|---|---|---|
| 2,702,552 A | 2/1955 | Moodie |
| 2,715,315 A | 8/1955 | Giardini |
| 3,307,553 A | 3/1967 | Liebner |
| 3,466,111 A | 9/1969 | Ring |

(List continued on next page.)

FOREIGN PATENT DOCUMENTS

| | | |
|---|---|---|
| DE | 195 21 003 C1 | 6/1995 |
| EP | 0 073 617 A1 | 3/1983 |
| EP | 0 164 751 A2 | 12/1985 |

(List continued on next page.)

OTHER PUBLICATIONS

Brigitte Dreno, MD., et al., "The Benefit of Chilling in Argon–Laser Treatment of Port–Wine Stains," vol. 75, No. 1, Chilling in Argon–Laser Treatment, pp. 42–45.
Barbara A. Gilchrest. et al., "Chilling Port Wine Stains Improves the Response to Argon Laser Therapy," Plastic and Reconstructive Surgery, vol. 69, No. 2, 1982, pp. 278–283.

(List continued on next page.)

*Primary Examiner*—David Shay
(74) *Attorney, Agent, or Firm*—Haverstock & Owens LLP (57) ABSTRACT

A selective aperture for a laser delivery system for providing incision, ablation and coagulation. A laser crystal disposed between two reflective surfaces forms a laser beam. An aperture member positioned between the laser crystal and one of the reflective surfaces includes a substantially circular aperture for passing the laser beam. The size of the aperture is selectively adjustable. The aperture member has a plurality of apertures of various different sizes and is rotatable about an axis of rotation. The axis of rotation is parallel to the longitudinal axis of the laser crystal. By appropriately rotating the aperture member, a selected one of the apertures is positioned to pass the laser beam. A stepper motor and flexible shaft are utilized for rotating the aperture member. At least one of the apertures is surrounded by a beveled portion of the rotatable member. Alternatively, two lasers with different size fixed apertures could be utilized and directed to a common surface. According to an aspect of the invention, an articulated arm is provided along with one or more refocussing optics for refocussing the laser beam as it travels through the arm. According to another aspect, a second laser source is provided along with a galvanometer for directing each of two laser beams to a surface to be treated. Such an arrangement provides exceptional versatility and control over the beam emitted. According to an another aspect, the aperture for a single laser source is rapidly changed during the performance of a procedure. By rapidly switching between forming an incision and cauterizing, an incision can be cauterized while being made.

36 Claims, 8 Drawing Sheets

U.S. PATENT DOCUMENTS

| | | |
|---|---|---|
| 3,538,919 A | 11/1970 | Meyer |
| 3,596,514 A | 8/1971 | Mefferd et al. |
| 3,693,623 A | 9/1972 | Harte et al. |
| 3,720,213 A | 3/1973 | Hobart et al. |
| 3,783,407 A | 1/1974 | Mefferd et al. |
| 3,821,510 A | 6/1974 | Muncheryan |
| 3,834,391 A | 9/1974 | Block |
| 3,854,153 A | 12/1974 | Fadler et al. |
| 3,868,592 A | 2/1975 | Yarborough et al. |
| 3,873,941 A | 3/1975 | Yarborough et al. |
| 3,900,034 A | 8/1975 | Katz et al. |
| 3,934,210 A | 1/1976 | Yarborough et al. |
| 3,967,627 A | 7/1976 | Brown |
| 3,973,825 A | 8/1976 | Starkweather |
| 3,995,166 A | 11/1976 | Hobart et al. |
| 4,006,299 A | 2/1977 | Grafton |
| 4,071,031 A | 1/1978 | Lowman |
| 4,122,853 A | 10/1978 | Smith |
| 4,140,130 A | 2/1979 | Storm, III |
| 4,143,660 A | 3/1979 | Malyshev et al. |
| 4,149,529 A | 4/1979 | Copeland et al. |
| 4,150,342 A | 4/1979 | Johnston, Jr. et al. |
| 4,174,154 A | 11/1979 | Kawasaki |
| 4,185,633 A | 1/1980 | Prozorov et al. |
| 4,240,431 A | 12/1980 | Komiya |
| 4,274,703 A | 6/1981 | Fisli |
| 4,276,520 A | 6/1981 | Rosenberg |
| 4,276,779 A | 7/1981 | Davis, Jr. |
| 4,313,093 A | 1/1982 | Suenaga et al. |
| 4,329,997 A | 5/1982 | de Yampert et al. |
| 4,373,816 A | 2/1983 | Laib |
| 4,378,600 A | 3/1983 | Hobart |
| 4,381,007 A | 4/1983 | Doss |
| RE31,279 E | 6/1983 | Mefferd et al. |
| 4,388,924 A | 6/1983 | Weissman et al. |
| 4,408,602 A | 10/1983 | Nakajima |
| 4,461,294 A | 7/1984 | Baron |
| 4,473,074 A | 9/1984 | Vassiliadis |
| 4,500,996 A | 2/1985 | Sasnett et al. |
| 4,503,854 A | 3/1985 | Jako |
| 4,516,564 A | 5/1985 | Koiso et al. |
| 4,538,181 A | 8/1985 | Taylor |
| 4,545,657 A | 10/1985 | Sunago |
| 4,559,942 A | 12/1985 | Eisenberg |
| 4,566,107 A | 1/1986 | Kitaura et al. |
| 4,608,978 A | 9/1986 | Rohr |
| 4,608,979 A | 9/1986 | Breidenthal et al. |
| 4,617,926 A | 10/1986 | Sutton |
| 4,660,798 A | 4/1987 | Kinoshita |
| 4,662,730 A | 5/1987 | Outwater et al. |
| 4,665,913 A | 5/1987 | L'Esperance, Jr. |
| 4,672,969 A | 6/1987 | Dew |
| 4,684,222 A | 8/1987 | Borrelli et al. |
| 4,733,660 A | 3/1988 | Itzkan |
| 4,753,503 A | 6/1988 | Day et al. |
| 4,761,047 A | 8/1988 | Mori |
| 4,785,456 A | 11/1988 | Kaplan |
| 4,791,927 A | 12/1988 | Menger |
| 4,819,669 A | 4/1989 | Politzer |
| 4,852,115 A | 7/1989 | Viherkoski |
| 4,856,513 A | 8/1989 | Muller |
| 4,864,578 A | 9/1989 | Proffitt et al. |
| 4,871,252 A | 10/1989 | Beni et al. |
| 4,887,019 A | 12/1989 | Reis et al. |
| 4,887,894 A | 12/1989 | Gluzerman et al. |
| 4,896,015 A | 1/1990 | Taboada et al. |
| 4,915,484 A | 4/1990 | Yamamoto |
| 4,939,739 A | 7/1990 | Hobart et al. |
| 4,941,093 A | 7/1990 | Marshall et al. |
| 4,949,358 A | 8/1990 | Kantorski et al. |
| 4,963,143 A | 10/1990 | Pinnow |
| 4,971,411 A | 11/1990 | Takanashi |
| 5,000,752 A | 3/1991 | Hoskin et al. |
| 5,023,886 A | 6/1991 | Hobart et al. |
| 5,033,061 A | 7/1991 | Hobart et al. |
| 5,046,184 A * | 9/1991 | Chee et al. ............ 372/18 |
| 5,052,017 A | 9/1991 | Hobart et al. |
| 5,055,048 A | 10/1991 | Vassiliadis et al. |
| 5,057,104 A | 10/1991 | Chess |
| 5,059,192 A | 10/1991 | Zaias |
| 5,061,062 A | 10/1991 | Schneiter |
| 5,098,426 A | 3/1992 | Sklar et al. |
| 5,123,028 A | 6/1992 | Hobart et al. |
| 5,123,845 A | 6/1992 | Vassiliadis et al. |
| 5,125,923 A | 6/1992 | Tanner et al. |
| 5,128,509 A | 7/1992 | Black et al. |
| 5,140,606 A | 8/1992 | Yarborough et al. |
| 5,152,759 A | 10/1992 | Parel et al. |
| 5,168,386 A | 12/1992 | Galbraith |
| 5,182,857 A | 2/1993 | Simon |
| 5,190,032 A | 3/1993 | Zacoi |
| 5,198,926 A | 3/1993 | Sheinis et al. |
| 5,207,576 A | 5/1993 | Vassiliadis et al. |
| 5,210,398 A | 5/1993 | Metlitsky |
| 5,226,907 A | 7/1993 | Tankovich |
| 5,227,910 A | 7/1993 | Khattak ............ 359/211 |
| 5,269,778 A | 12/1993 | Rink et al. |
| 5,275,564 A | 1/1994 | Vassiliadis et al. ...... 433/226 |
| 5,282,797 A | 2/1994 | Chess ............... 606/9 |
| 5,292,320 A | 3/1994 | Brown et al. ............ 606/15 |
| 5,300,066 A | 4/1994 | Manoukian et al. |
| 5,312,398 A | 5/1994 | Hobart et al. |
| 5,335,242 A | 8/1994 | Hobart et al. |
| 5,344,418 A | 9/1994 | Gharffari ............ 606/9 |
| 5,359,669 A | 10/1994 | Shanley et al. ............ 382/6 |
| 5,360,447 A | 11/1994 | Koop ............... 623/15 |
| 5,375,132 A | 12/1994 | Connors et al. |
| 5,405,368 A | 4/1995 | Eckhouse |
| 5,411,502 A | 5/1995 | Zair ............... 606/10 |
| 5,413,555 A | 5/1995 | McMahan ............ 606/4 |
| 5,421,819 A | 6/1995 | Edwards et al. ............ 604/22 |
| 5,423,801 A | 6/1995 | Marshall et al. ............ 606/5 |
| 5,425,727 A | 6/1995 | Koziol ............ 606/5 |
| 5,425,728 A | 6/1995 | Tanovich ............ 606/9 |
| 5,426,662 A | 6/1995 | Mefferd et al. |
| 5,464,013 A | 11/1995 | Lemelson ............ 128/655.01 |
| 5,474,549 A | 12/1995 | Oritz et al. |
| 5,480,396 A | 1/1996 | Simon et al. ............ 606/4 |
| 5,486,172 A | 1/1996 | Chess ............... 606/20 |
| 5,520,679 A | 5/1996 | Lin ............... 606/5 |
| 5,531,740 A | 7/1996 | Black |
| 5,540,676 A | 7/1996 | Freiberg |
| 5,546,214 A | 8/1996 | Black et al. ............ 359/203 |
| 5,582,752 A | 12/1996 | Zair ............ 219/121.85 |
| 5,585,698 A | 12/1996 | Langhans et al. |
| 5,595,568 A | 1/1997 | Anderson et al. ............ 606/9 |
| 5,611,795 A | 3/1997 | Slatkine et al. ............ 606/9 |
| 5,618,285 A | 4/1997 | Zair |
| 5,620,435 A | 4/1997 | Belkin et al. |
| 5,620,478 A | 4/1997 | Eckhouse |
| 5,624,437 A | 4/1997 | Freeman et al. ............ 606/12 |
| 5,626,631 A | 5/1997 | Eckhouse |
| 5,637,850 A | 6/1997 | Honda ............ 235/454 |
| 5,642,287 A | 6/1997 | Sotiropoulos et al. . 364/474.08 |
| 5,643,334 A | 7/1997 | Eckhouse et al. |
| 5,645,550 A | 7/1997 | Hohla ............ 606/108 |
| 5,651,784 A | 7/1997 | Kloptek |
| 5,655,547 A | 8/1997 | Karni |
| 5,659,563 A | 8/1997 | Reed et al. |
| 5,662,643 A | 9/1997 | Kung et al. |
| 5,662,644 A | 9/1997 | Swor |

| | | | |
|---|---|---|---|
| 5,735,844 A | 4/1998 | Anderson et al. | 606/9 |
| 5,756,981 A | 5/1998 | Roustaei et al. | 235/462 |
| 5,769,787 A | 6/1998 | Lemelson | 600/407 |
| 5,770,847 A | 6/1998 | Olmstead | 235/46.2 |
| 5,782,822 A | 7/1998 | Telfair et al. | 606/5 |
| 5,783,798 A | 7/1998 | Abraham | 219/121.73 |
| 5,814,803 A | 9/1998 | Olmstead et al. | 235/462 |
| 5,814,827 A | 9/1998 | Katz | 250/556 |
| 5,846,080 A | 12/1998 | Schneider | 433/215 |
| 5,849,006 A | 12/1998 | Frey et al. | 606/5 |
| 5,865,830 A | 2/1999 | Parel et al. | 606/5 |
| 5,868,731 A | 2/1999 | Budnik et al. | 606/9 |
| 5,883,658 A | 3/1999 | Schubert et al. | 347/258 |
| 5,900,963 A | 5/1999 | Li et al. | 359/205 |
| 5,931,848 A | 8/1999 | Saadat | 606/167 |
| 5,933,268 A | 8/1999 | Li et al. | 359/207 |
| 5,938,657 A | 8/1999 | Assa et al. | |
| 5,941,893 A | 8/1999 | Saadat | 606/180 |
| 5,997,531 A | 12/1999 | Loeb et al. | 606/13 |
| 6,066,127 A | 5/2000 | Abe | 606/2 |
| RE36,872 E | 9/2000 | Zair | |
| 6,162,213 A * | 12/2000 | Stewart | 606/10 |
| 6,228,075 B1 | 5/2001 | Furumoto | 606/9 |
| 6,228,076 B1 | 5/2001 | Winston et al. | 606/11 |
| 6,267,771 B1 | 7/2001 | Tanovich et al. | 606/131 |

FOREIGN PATENT DOCUMENTS

| | | |
|---|---|---|
| EP | 0 714 642 A1 | 6/1996 |
| EP | 0 755 698 A2 | 1/1997 |
| JP | 56-166123 | 12/1981 |
| WO | WO 86/02783 | 5/1986 |
| WO | WO 92/18057 | 10/1992 |
| WO | WO 93/03521 | 2/1993 |
| WO | WO 95/15725 | 6/1995 |
| WO | WO 96/34566 | 11/1996 |
| WO | WO 96/41577 | 12/1996 |

OTHER PUBLICATIONS

Akira Yanai, M.D. et al., "Argon Laser Therapy of Port–Wine Stains: Effects and Limitations," vol. 75, No. 4, Apr. 1985, pp. 520–525.

Leon Goldman, MD., et al., "Replica Microscopy and Scanning Electron Microscopy of Laser Impacts on the Skin," The Journal of Investigative Dermatology, vol. 52, No. 1, pp. 18–24.

Melanie C. Grossman M.D., et al., "Damage to hair follicles by normal–mode ruby laser pulses," Journal of the American Academy of Dermatology, Dec. 1996, pp. 889–894.

Luigi L. Polla MD., et al., "Melanosomes Are a Primary Target of Q–Switched Ruby Laser Irradiation in Guinea Pig Skin," The Society for Investigative Dermatology, Inc., vol. 89, No. 3, 1987, pp. 281–286.

"The Journal of Investigate Dermatology," Apr. 1987, vol. 88, No. 4, pp. 523.

M. Douglas Gossman, MD., et al., "Prospective Evaluation of the Argon Laser in the Treatment of Trichiasis," Mar. 1992, vol. 23, No. 3, 183–187.

R. Rox Anderson et al., "The Optics of Human Skin," The Journal of Investigative Dermatology 77, 1981, pp. 13–19.

Leon Goldman M.D. et al., "Treatment of Basal Cell Epithelioma by Laser Radiation," Epithelioma–Goldman & Wilson, 1961, vol. 189, No. 10, pp. 773–775.

Leon Goldman MD., et al., "Laser Action as the Cellular Level," Multidiscipline Research Forum, JAMA, Nov. 7, 1996, vol. 198, No. 6, pp. 641–644.

Leon Goldman MD., et al. "Biomedical Aspects of Lasers" JAMA, Apr. 20, 1964, vol. 188, No. 3, pp. 302–306.

Leon Goldman MD., et al., "Effect of the Laser Beam on the Skin," Preliminary Report, 2 pgs.

Leon Goldman MD., et al., "Effect of the Laser Beam on the Skin," III. Exposure of Cytological Preparations, pp. 247–251.

"Pathology of the Effect of the Laser Beam on the Skin," Nature, Mar. 2, 1963, vol. 197, pp. 912–914.

"Preliminary Investigation of Fat Embolization from Pulsed Ruby Laser Impacts of Bone," Nature, vol. 221, Jan. 1969, pp. 361–363.

Leon Goldman MD., et al., "Radiation from a Q–Switched Ruby Laser: Effect of Repeated Impacts of Power Output of 10 Megawatts on a Tattoo of Man," pp. 69–71.

Kaufman et al., "Pulsed Er: YAG–and 308 nm UV–Excimer Laser: An in Vitro and In Vivo Study of Skin–Ablative Effects", Lasers in Surgery and Medicine, vol. 9, 1989, p. 132–140, US.

Zweig et al., "A Comparative Study of Laser Tissue Interaction at 2.94µ and 10.6 µm", Applied Physics B, vol. 47, 1988, p. 259–265.

Burkhardt et al., "Are More Passes Better? Safety versus Efficacy with the Pulsed $CO_2$ Laser ", Plastic and Reconstructive Surgery, vol. 100, No. 6, Nov. 1997, p. 1531–1534, US.

Walsh et al., "Er:YAG Laser Ablation of Tissue: Measurement of Ablation Rates", Lasers in Surgery and Medicine, vol. 9, 1989 p. 327–337, US.

Walsh et al., "Er:.YAG Laser Ablation of Tissue: Effect of Pulse Duration and Tissue Type on Thermal Damage", Lasers in Surgery and Medicine, vol. 9, 1989, p. 314–326, US.

Hohenleutner et al., "Fast and Effective Skin Ablation With an Er:.YAG Laser: Determination of Ablation Rates and Thermal Damage Zones", Lasers in Surgery and Medicine, vol. 20, 1997, p. 242–247, US.

Hibst et al., "Effects of Laser Parameters on Pulsed Er–YAG Laser Skin Ablation", Lasers in Medical Science, vol. 6, 1991, p. 391–397, US.

Drnovsek–Olup et al., "Use of Er:.YAG Laser for Bengin Skin Disorders", Lasers in Surgery and Medicine, vol. 21, 1997, p. 13–19, US.

Herdman et al., "An in vitro comparision of the Erbium:YAG laser and the carbon dioxide laser in laryngeal surgery", The Journal of Laryngology and Otology, vol. 107, 1993, p. 908–911, US.

Walsh et al., "Pulsed $CO_2$ Laser Tissue Ablation: Measurement of the Ablation Rate", Lasers in Surgery and Medicine, vol. 8, 1988, p. 264–275, US.

Walsh et al., "Effect of Tissue Type and Pulse Duration on Thermal Damage", Lasers in Surgery and Medicine, vol. 8, 1998, p. 108, 111–118.

Walsh et al., "Pulsed $CO_2$ Laser Ablation of Tissue: Effect of Mechanical Properties", Transactions on Biomedical Engineering, vol. 36, Dec. 1989, p. 1195–1201, US.

Ross et al., "Effects of Heterogeneous Absorption of Laser Radiation in Biotissue Ablation: Characterization of Ablation of Fat With a Pulsed $CO_2$ Laser", Laser in Surgery and Medicine, vol. 21, 1997, p. 59, 61–64.

Sabbagh, "Erbium Laser Gaining Popularity for Cosmetic Applications", Medical Laser Report, Nov. 1996, p. 2–3, US.

Anderson et al., "Selective Photothermolysis: Precise Microsurgery by Selective Absorption of Pulsed Radiation," Science, vol. 220, Apr. 1983, pp. 524–527, US.

* cited by examiner

SELECTIVE APERTURE FOR LASER DELIVERY SYSTEM FOR PROVIDING INCISION, TISSUE ABLATION AND COAGULATION

RELATED APPLICATION

This application claims priority under 35 U.S.C. §119(e) of the U.S. provisional application Ser. No. 60/118,635 filed on Feb. 4, 1999 and entitled "Selective Aperture For Laser Delivery System For Providing Incision, Tissue Ablation And Coagulation." The provisional application Ser. No. 60/118,635 filed on Feb. 4, 1999 and entitled "Selective Aperture. For Laser Delivery System For Providing Incision, Tissue Ablation And Coagulation" is also hereby incorporated by reference. This application is also a continuation-in-part of U.S. patent application Ser. No. 09/018,104, filed Feb. 3, 1998, and entitled "Dual Mode Laser Delivery System Providing Controllable Depth Of Tissue Ablation And Corresponding Controllable Depth Of Coagulation," which is hereby incorporated by reference.

FIELD OF THE INVENTION

The present invention relates to the field of medical lasers. More particularly, the present invention relates to the field of medical lasers for effecting incisions, tissue ablation and coagulation.

BACKGROUND OF THE INVENTION

A laser beam is formed when a material capable of lasing, such as a solid-state crystal or gas, is excited by incident light energy. In response, ions within the material are pumped to a high energy level and, then, energy is dissipated when the ions return to a ground state. In transitioning from the high energy level to the ground state, the ions each emit a photon in addition to heat energy. The emitted photons have a uniform wavelength ($\lambda$) and eventually form the laser beam.

Figure 1:
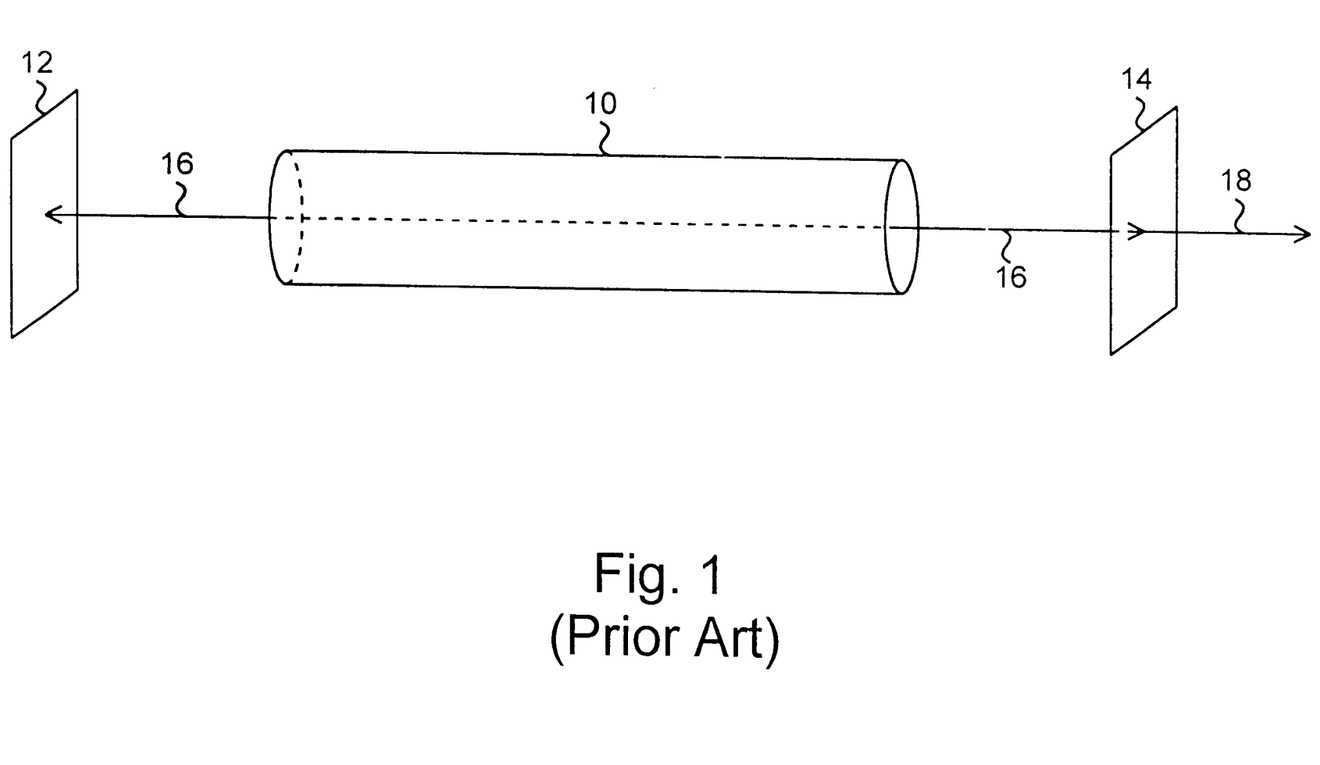
FIG. 1 illustrates a typical solid state laser in accordance with the prior art.

FIG. 1 schematically illustrates a solid state laser in accordance with the prior art. A cylindrical rod-shaped crystal 10 is disposed between two reflective surfaces 12, 14. The surfaces 12, 14 are aligned parallel to one another and perpendicular to the longitudinal axis of the crystal 10. While light can be emitted from the crystal 10 in various different directions, only a coherent beam of light 16 which travels along the axis of the crystal 10 is reflected between the surfaces 12, 14. The surface 12 has a reflectivity of nearly 100% and, thus, reflects all of the beam 16. The surface 14, however, has a reflectivity of less than 100% and a transmissivity of greater than zero. Thus, a portion 18 of the beam 16 passes through the surface 14. The emitted beam 18 can be utilized for industrial or medical applications. For example, the beam 18 can be directed to a target surface.

Figure 2:
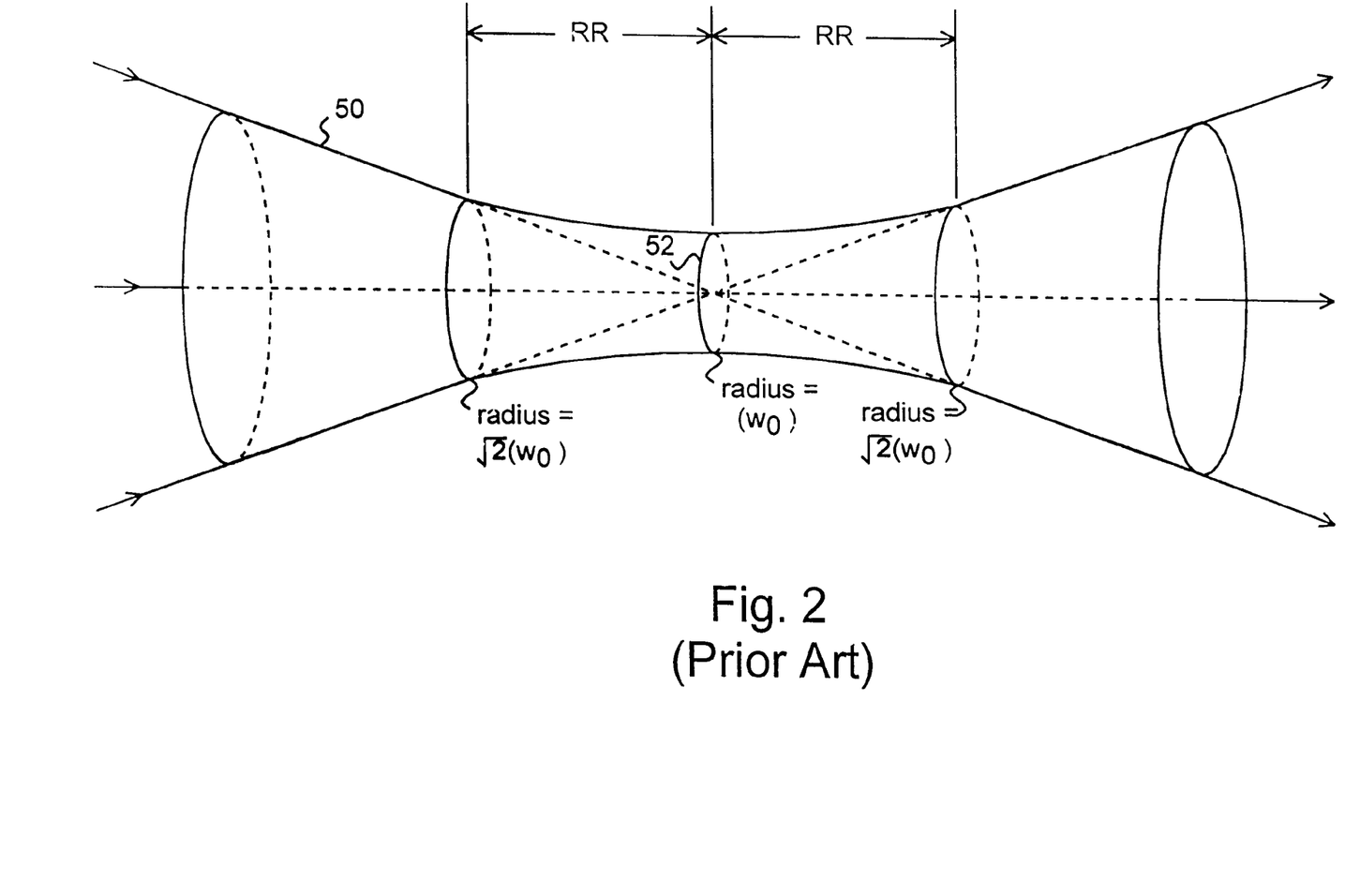
FIG. 2 illustrates a laser beam converging to a waist and, then, diverging from the waist.

A property of a laser beam is that the beam is continually diffracting. This diffraction is evidenced by convergence (narrowing) to a waist or divergence from a waist. FIG. 2 schematically illustrates a laser beam 50 converging to a waist 52 and, then, diverging from the waist 52. The waist 52, whose radius is given as $\omega_0$, is the narrowest portion of the beam 52. A distance known as the Rayleigh Range (RR), is a distance from the waist 52 that the beam 50 achieves a radius given by the square root of two times $\omega_0$ ($1.414\omega_0$). Thus, the Rayleigh Range is a measure of the convergence and divergence of the beam 50. An important relationship which holds for the beam 50 is given by:

$$RR = \frac{\pi \omega_0^2}{M^2 \lambda}$$

where M is a constant which characterizes the number of times greater than the diffraction limit is the beam 52. As can be seen from this equation, for a given waist, the Rayleigh Range is longest when M is equal to one. Similarly, for a given Rayleigh Range, the waist is at its most narrow when M is equal to one. The constant M, however, can be greater than one.

Figure 3A:
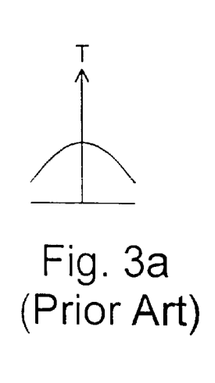
FIG. 3a illustrates a first parabolic plot of temperature (T) of a laser crystal vs. transverse distance (X) from the center of the crystal.
Figure 3B:
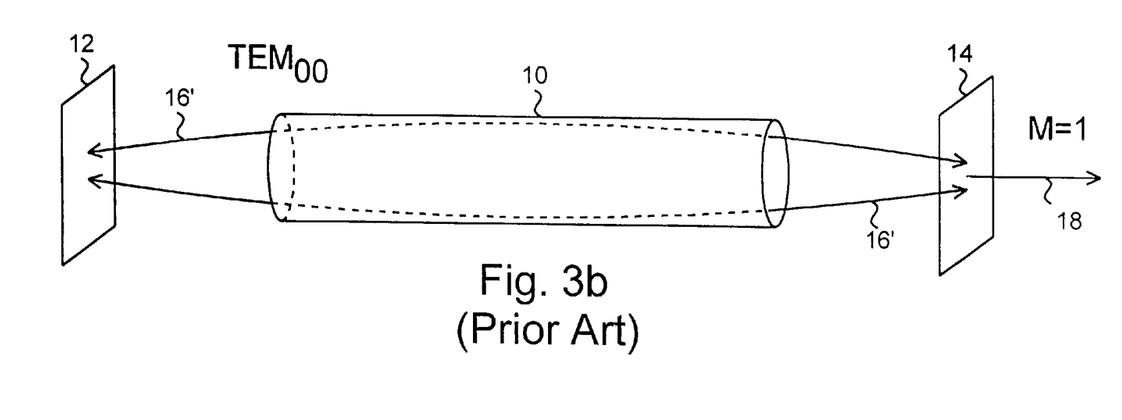
FIG. 3b illustrates the effects of a thermal lens formed by the temperature gradient of FIG. 3a on the solid state laser of FIG. 1 where the constant M for the laser beam is one.

As mentioned, when the excited ions of the crystal 10 (FIG. 1) return from an excited state to the ground state, heat is dissipated, in addition to a photon. To avoid excessive heat from building up in the crystal 10, this heat is typically removed by a cooling jacket which surrounds the crystal 10. As a result of removing heat from the crystal 10, the temperature of the crystal is higher in the center than near the outer edges. As shown in FIG. 3a, when the temperature (T) of the crystal 10 is plotted along a vertical axis and distance (X) from the center of the crystal 10 is plotted along a horizontal axis, a parabolic curve results. The refractive index of the crystal 10, however, varies with temperature. As a result, the crystal 10 behaves as a lens (a thermal lens). This thermal lens tends to narrow the beam 16' at its ends, as schematically shown in FIG. 3b, thereby counter-acting the natural tendency for the beam to diverge, as illustrated in FIG. 2. FIG. 3b illustrates the effects of a thermal lens on the solid state laser of FIG. 1 where the constant M for the beam 16' is one. When the constant M is equal to one, the beam 16' is considered to be of mode $TEM_{00}$. For the emitted beam 18, M is also equal to one.

Figure 4A:
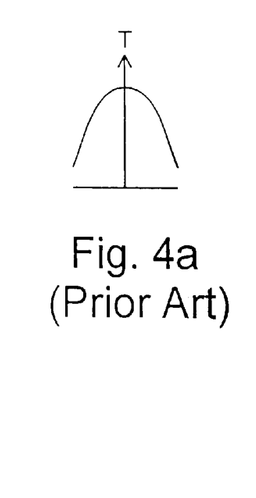
FIG. 4a illustrates a second parabolic plot of temperature (T) of a laser crystal vs. distance (X) from the center of the crystal.
Figure 4B:
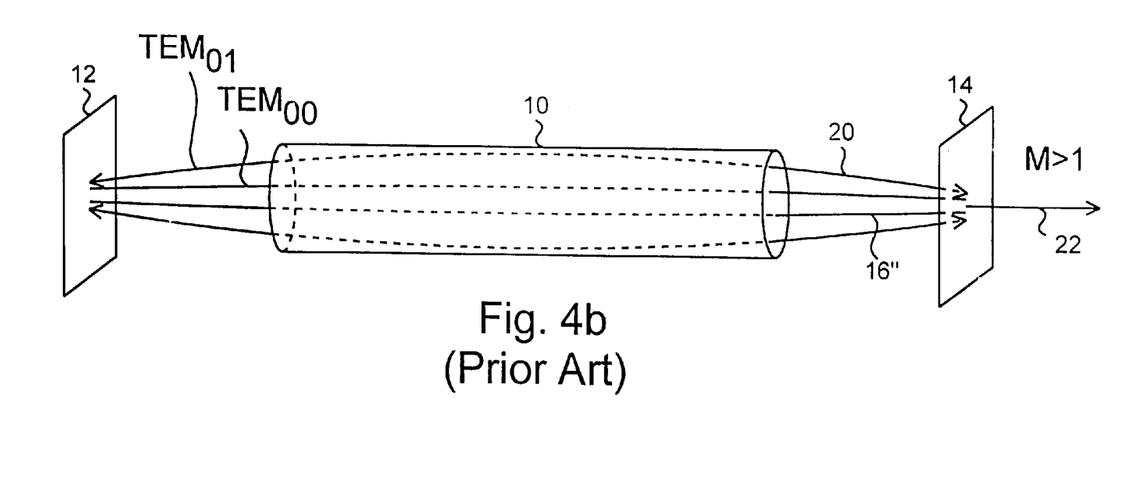
FIG. 4b illustrates the effects of a thermal lens formed by the temperature gradient of FIG. 4a on the solid state laser of FIG. 1 where the constant M for the laser beam is greater than one.

Under operating conditions where the temperature in the center of the crystal 10 is increased, as shown in FIG. 4a, the effect of the thermal lens is to further narrow the mode $TEM_{00}$ beam 16". FIG. 4b schematically illustrates the effects of increasing temperatures in the solid state laser of FIG. 1. Note that in FIG. 4b, the $TEM_{00}$ beam 16" does not pass through the outermost portions of the crystal 10. Light emitted from these regions, forms a beam 20 of another mode (e.g., $TEM_{01}$). The constant M for the beam 20 of mode $TEM_{01}$ is 1.4. A beam 22 which emits from the laser shown in FIG. 4b has a constant M which is between 1 and 1.4. Further increases in the strength of the thermal lens results in increasing values for the constant M of the beam 22.

Lasers are used in medical procedures to rejuvenate, restore and resurface skin damaged due to many causes including prolonged exposure to the sun. Laser energy is delivered to the surface of the skin in a controlled pattern in order to ablate or burn away layers of the skin. As the layers of skin grow back within the area of skin exposed to the laser, the skin is effectively resurfaced. To avoid excessive bleeding, it is important that a zone of thermal necrosis or coagulation is formed within the newly exposed tissue. In addition, lasers are used for vision correction by reshaping the lens in the eye. Lasers are also used for forming incisions by ablating a narrow band of tissue.

For each of these functions, the intensity and distribution of the laser beam, its wavelength, and the duration of exposure, all must be understood and/or appropriately controlled so that the desired results are achieved. Advances in laser apparatus have been directed to the difficulty in controlling these factors.

U.S. Pat. No. 4,791,927 discloses a dual-wavelength laser scalpel. A short wavelength blue light cuts the target tissue and a longer-wavelength red light cauterizes. The two wavelengths are formed as the fundamental frequency and second harmonic of a single laser source.

U.S. Pat. No. 5,651,784 discloses a rotatable aperture apparatus and methods for selective photoablation of surfaces. The intensity distribution of a beam of radiation is modified by inserting a rotatable mask into the beam. The mask is formed with one or more apertures that have a geometric spiral shape originating substantially from the center of rotation of the mask. A beam of radiation incident on the rotating mask is transmitted therethrough with intensity that varies as a function of radial position with respect to the rotation point.

U.S. Pat. No. 4,887,019 discloses a device for the generation of a laser beam spot of adjustable size on an object, in particular, in the human eye. A focusing device projects the laser beam onto the eye with a small focusing spot and a large aperture cone. A deflector device moves the focusing spot over the desired beam spot in a predetermined scanning pattern.

U.S. Pat. No. 4,941,093 discloses surface erosion using lasers for eroding a surface, such as a patient's cornea. A laser beam exits an optical system and is incident on the surface. An iris is placed in the beam between the optical system and the surface which can be opened while pulsing the beam so as to erode the center of the surface to a greater extent than the surrounding area. However, this patent teaches that iris diaphragms are undesirable because the shape of the opening can change along with its size. Thus, an alternative system is disclosed in U.S. Pat. No. 4,941,093 in which a beam shaping stop is placed between the optical system and the surface. The beam shaping stop is arranged to move along the beam axis in a direction of convergence or divergence of the beam.

What is needed is a method and apparatus for controlling the delivery of laser energy. What is further needed is a method and apparatus for controlling the delivery of laser energy for performing medical procedures.

SUMMARY OF THE INVENTION

The invention is a selective aperture for a laser delivery system for providing incision, ablation and coagulation. A laser crystal is disposed between two reflective surfaces for forming a laser beam. Preferably, the laser is an erbium YAG laser. An aperture member is positioned between the laser crystal and one of the reflective surfaces. The aperture member includes a substantially circular aperture for passing the laser beam. The size of the aperture is selectively adjustable. As a result, the waist and Rayleigh Range of the beam can be altered to suit the particular procedure being performed. Preferably, the aperture member has a plurality of apertures of various different sizes. In which case, the aperture member is rotatable about an axis of rotation. The axis of rotation is parallel to the longitudinal axis of the laser crystal. By appropriately rotating the aperture member, a selected one of the plurality of apertures is positioned to pass the laser beam. A stepper motor and flexible shaft can be utilized for rotating the aperture member. Preferably, at least one of the apertures is surrounded by a beveled portion of the rotatable member. The beveled portion is cone shaped and can have a cone angle of at least 100 degrees.

According to an aspect of the invention, an articulated arm is provided along with one or more refocussing optics for refocussing the laser beam as it travels through the arm. According to another aspect, a second laser source is provided along with a galvanometer for directing each of two laser beams to a surface to be treated. Such an arrangement provides exceptional versatility and control over the beam emitted. For example, one of the laser sources can be configured for a small waist size for forming an incision, while the other can be configured for a larger waist size for cauterizing the incision. By switching back and forth between pulses from each of the two lasers an incision can be cauterized concurrently as it is being made. Alternately, one of the lasers can be configured for ablating skin while the other is configured for performing coagulation. Additionally, one laser source could be configured for forming a precise incision and another for large area tissue ablation.

According to an another aspect of the invention, the aperture for a single laser source is rapidly changed during the performance of a procedure (i.e. "on-the-fly'). For example, by rapidly switching between forming an incision and cauterizing as the laser beam is pulsed, the laser system can cauterize an incision while it is being made. Although the functions are performed successively, by rapidly switching back and forth between appropriate apertures (time-division-multiplexing) in relation to the speed at which the incision is being made, the functions are effectively performed concurrently.

DETAILED DESCRIPTION OF THE PREFERRED EMBODIMENT

Figure 5:
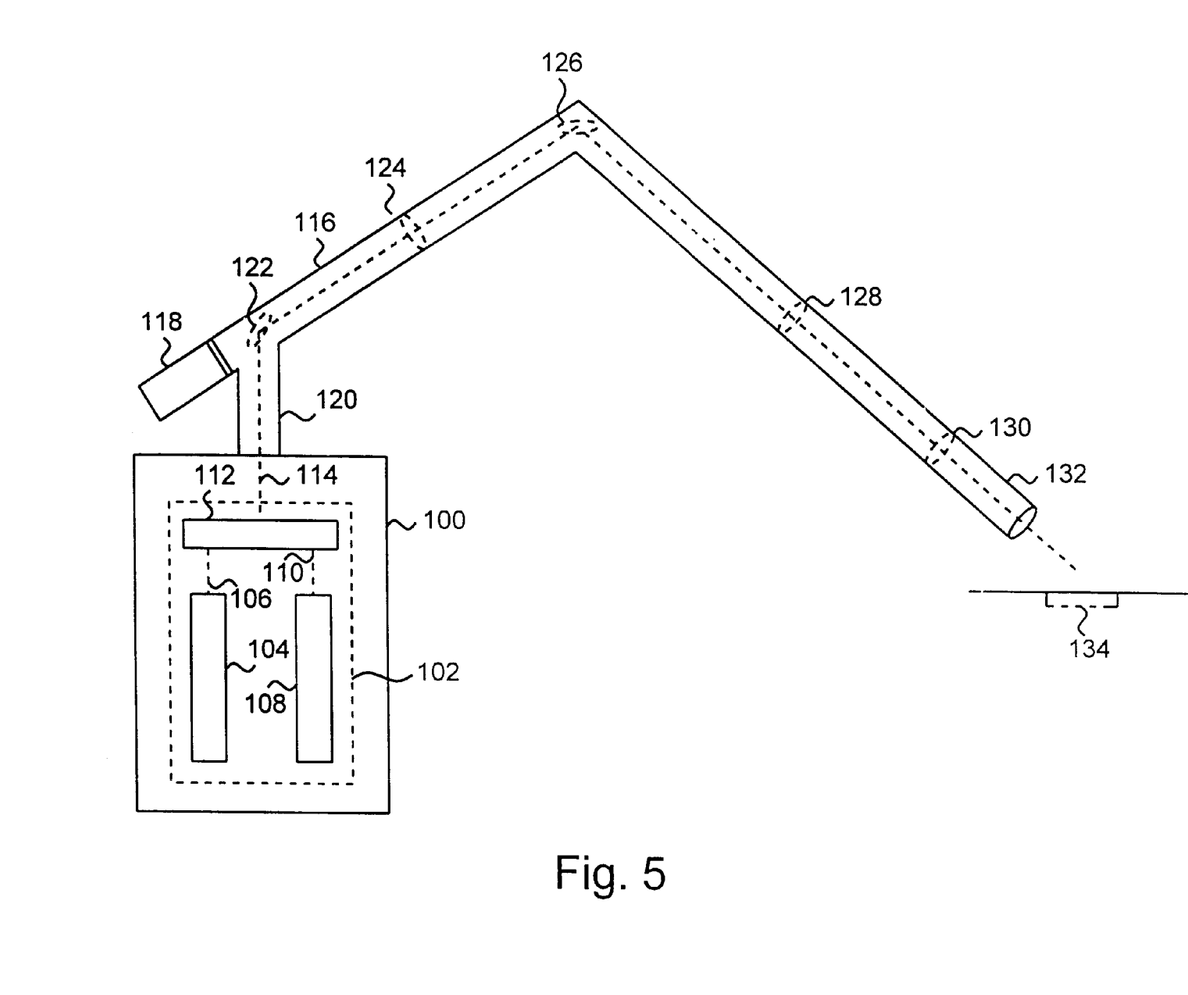
FIG. 5 illustrates a laser system in accordance with the present invention.

A laser system in accordance with the present invention is schematically illustrated in FIG. 5. A laser generation system housing 100 includes a laser source 102 from which a laser beam 114 is provided. The laser source 102 preferably includes two erbium lasers 104 and 108 which generate the laser beams 106 and 110, respectively. Alternatively, another appropriate laser source can be used within the system of the present invention. The two laser beams 106 and 110 are combined into the single laser output 114 by a galvanometer 112 which is a high speed scanning mirror that switches between the two laser outputs 106 and 110. The galvanometer 112 then provides the laser output 114 from the laser source 102. An articulated delivery arm 116 is mounted onto the laser generation system housing 100 and directs the laser output 114 from the laser source 102 through the arm 116, to a scanner handpiece 132 where it is delivered to a surface 134 which is to be treated.

The articulated arm 116 includes a weighted counterbalance 118 in order to reduce the weight necessary for the clinician to support during use. As will be described in further detail below, the articulated arm 116 also includes a number of lenses 124, 126, 128, 130 for conditioning the laser output 114 as it is directed through the arm 116. The laser output 114 is directed from the laser source 102 to a first series of directing optics 122, which are preferably turning mirrors, to direct the laser output 114 through the arm 116 towards a joint in the arm 116. From the first directing series of lenses 122, the laser output 114 travels through a first focusing lens 124 to a second directing series of lenses 126 which direct the laser output 114 through the joint of the arm towards the scanner handpiece 132. From the second directing series of lenses 126, the laser output 114 travels through focussing lenses 128 and 130. From the focussing lens 130, the laser output 114 travels through the scanner handpiece 132 and is provided to the surface 134 to be treated. The focusing lenses 124, 128 and 130 can be simple convex lenses.

Figure 6:
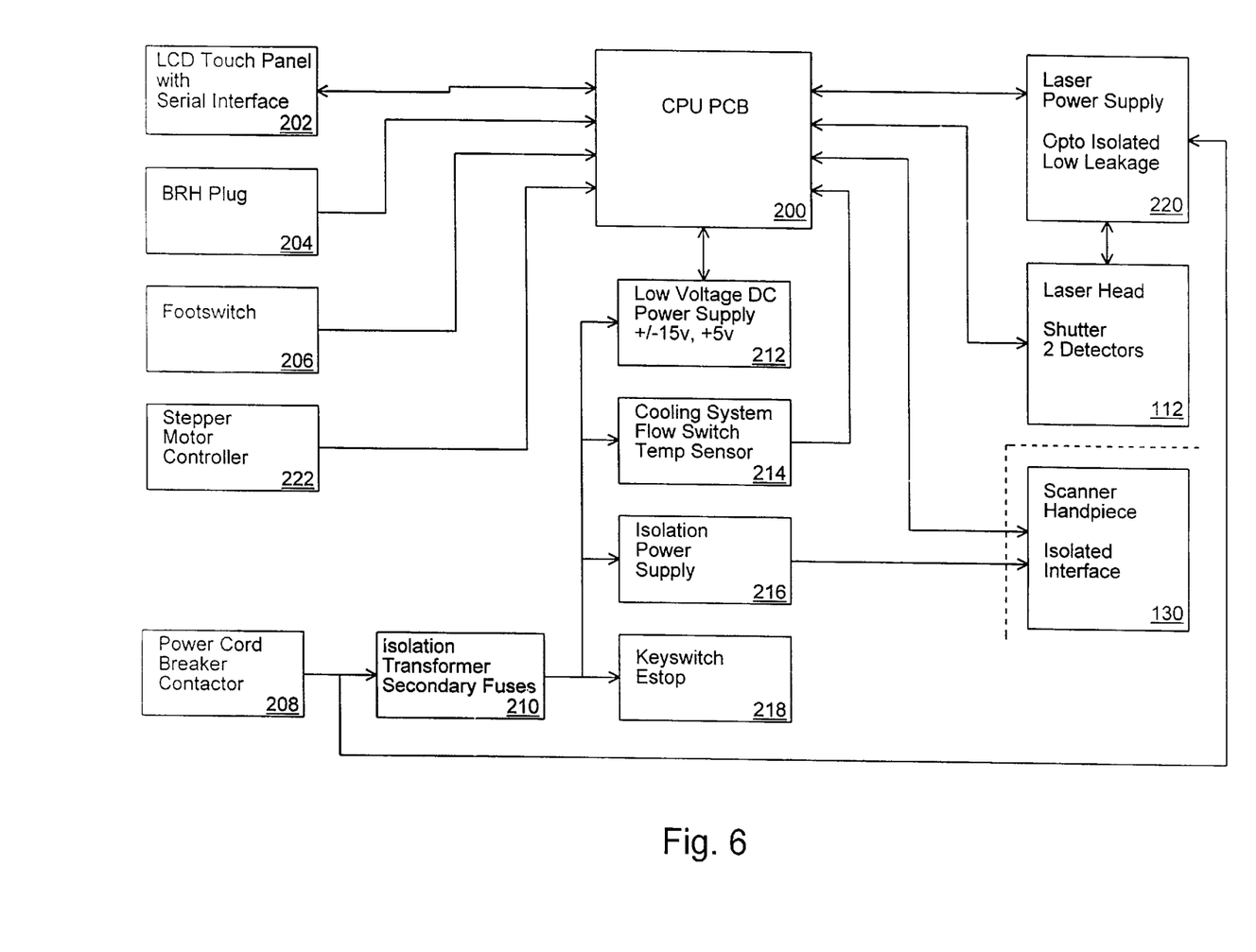
FIG. 6 illustrates a block diagram of the electrical components and connections within the laser system in accordance with the present invention.

A block diagram of the electrical components and connections within the laser system of the preferred embodiment of the present invention is illustrated in FIG. 6. An LCD touch panel 202 is coupled to a central processing unit (CPU) 200. The LCD touch panel 202 provides a graphical user interface to the user to provide communications to the user and to receive input commands from the user for operation of the laser system. Through this LCD panel 202 the user is provided with a display of current settings and has the ability to change settings by touching appropriate locations on the touch panel. As will be apparent to those skilled in the art, any other appropriate display and input device could alternatively be used within the laser system of the present invention. A footswitch 206 is also coupled to the CPU 200 and is used by the user to control operation of the laser system in a known manner. A safety interlock plug 204 is coupled to the CPU to allow for connection of an access door to the housing 100 (FIG. 5) or other interlock to the system. If the interlock is broken the laser is disabled.

A power cord 208 is coupled to provide power to the laser system of the present invention. The power cord 208 is coupled to an isolation transformer 210 and to a laser power supply 220 for providing power to components within the laser system. The isolation transformer 210 is coupled to provide power to a keyswitch 218, an isolation power supply 216, a cooling system 214 and a low voltage DC power supply 212. The cooling system 214 monitors the temperature within the laser system and operates in order to maintain the temperature within an acceptable operating range. The cooling system 214 is also coupled to the CPU 200. The low voltage DC power supply 212 is coupled to provide power to the CPU 200.

The laser power supply 220 is coupled to the CPU 200 and to the laser head or galvanometer 112 (FIG. 5) from which the laser output 114 (FIG. 5) is provided. Preferably, the laser power supply 220 is optically isolated from the other electrical sub-systems in order to insure patient safety and prevent patient exposure to any leakage from the high voltage laser power supply 220. The laser head 112 is also coupled to the CPU 200. The scanner handpiece 132 (FIG. 5) is coupled to receive power from the isolation power supply 216. The scanner handpiece 132 is also coupled to the CPU 200.

Figure 9:
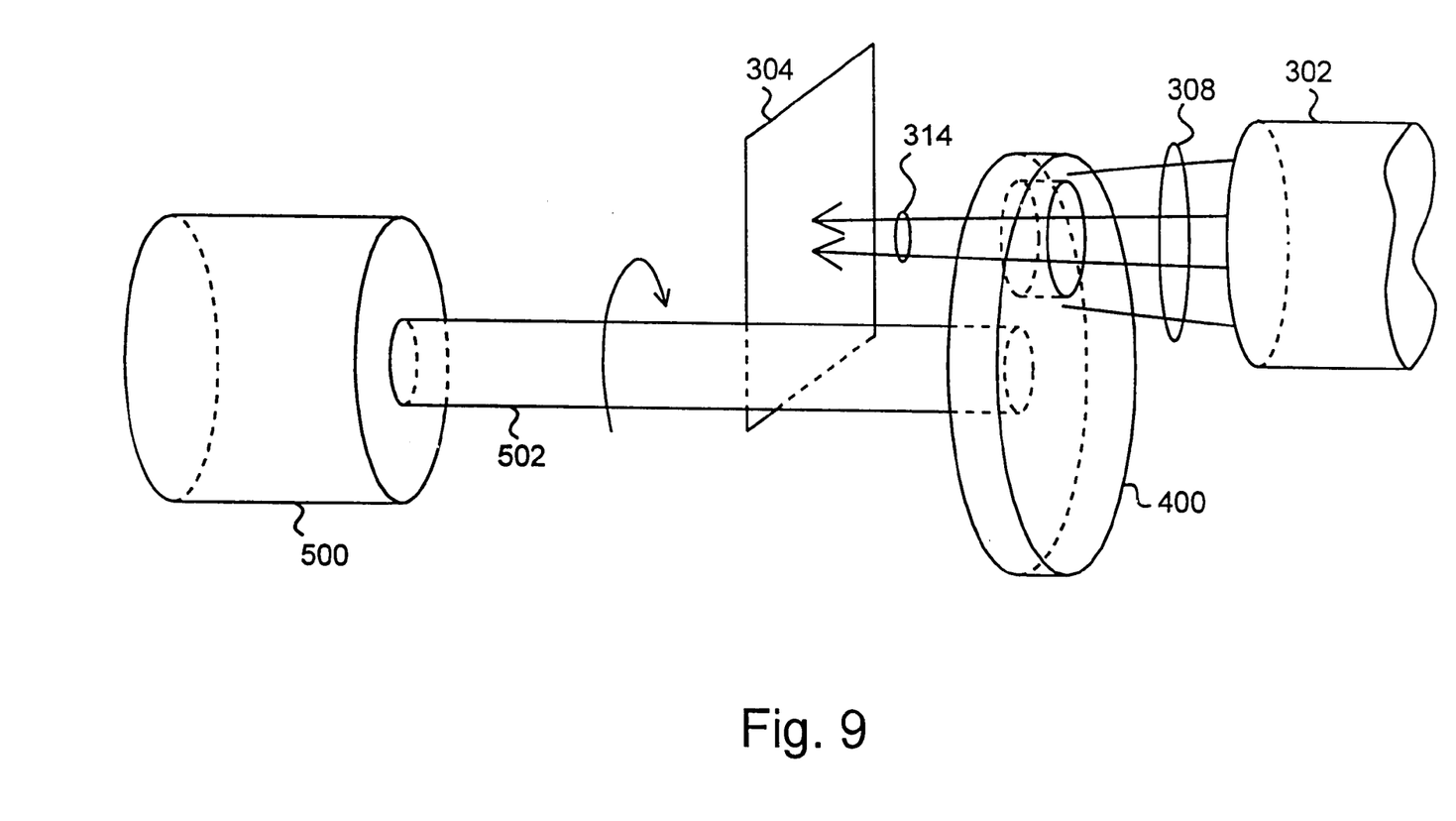
FIG. 9 illustrates the rotatable wheel in addition to a stepper motor for adjusting the aperture in accordance with the present invention.

The laser system illustrated in FIG. 6 also includes a stepper motor controller 222 coupled to the CPU 200 for controlling a stepper motor 500 (FIG. 9). As explained herein, the stepper motor 500 controls an aperture utilized by the laser system in forming the beam 114 (FIG. 5).

Figure 7:
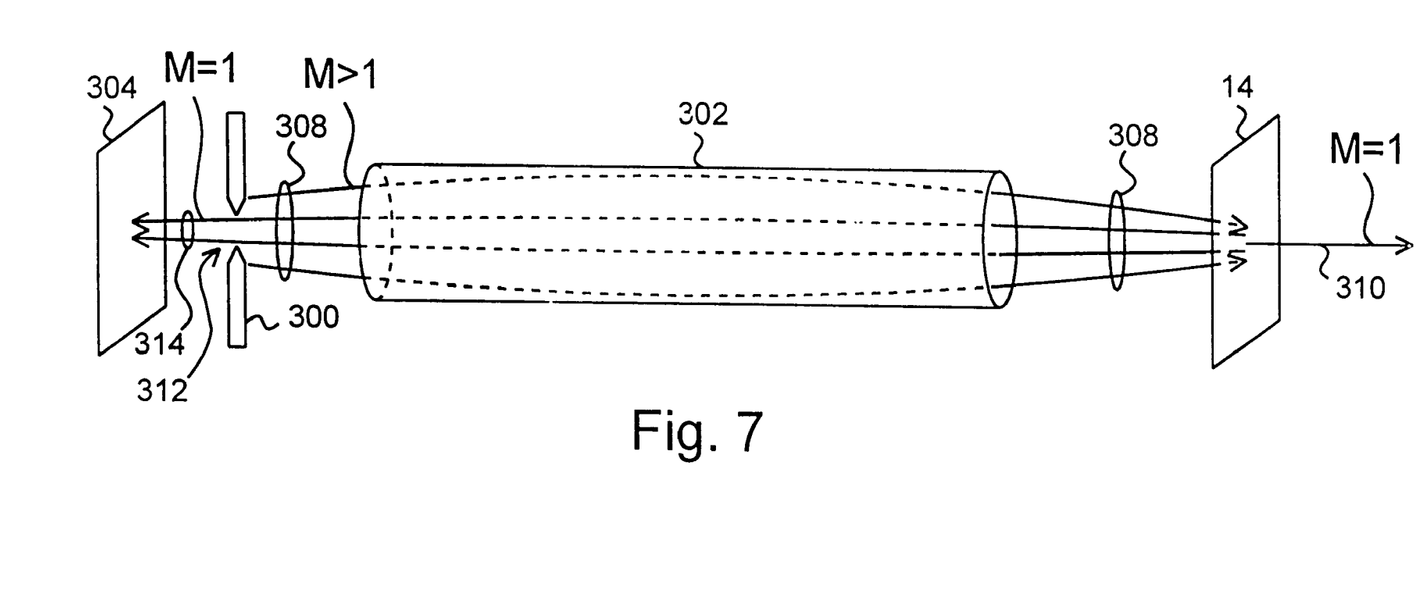
FIG. 7 illustrates a laser having a selective aperture in accordance with the present invention.

FIG. 7 schematically illustrates a laser having a selectively adjustable aperture member 300 in accordance with the present invention. A cylindrical rod-shaped crystal 302 is disposed between two reflective surfaces 304, 306. The surfaces 304, 306 are aligned parallel to one another and perpendicular to the longitudinal axis of the crystal 302. Light 308 emitted from the crystal 302 travels along the axis of the crystal 302 and is reflected between the surfaces 304, 306. The surface 304 has a reflectivity of nearly 100% and, the surface 306 has a reflectivity of less than 100% (e.g., 90%) and a transmissivity of greater than zero (e.g., 10%). Thus, a portion 310 of the beam 308 passes through the surface 306. The emitted beam 310 can be utilized for industrial or medical applications. For example, the beam 310 can be guided by a series of lenses to a target surface for forming an incision, performing tissue ablation, cauterization or coagulation.

The aperture member 300 includes an aperture 312. The aperture 312 is preferably substantially circular and is aligned with the crystal 302 such that the center of the aperture 312 is aligned with the central axis of the crystal 302. The diameter of the aperture 312 controls the mode of the light which is reflected between the surfaces 304, 306 according to its diameter. For example, the aperture 312 allows a portion 314 of the light 308 to strike the reflective surface 304, while the aperture member 300 blocks the remaining light 308. The diameter of the aperture 310 is preferably selectively adjustable. For example, the aperture 312 can be adjusted to pass light of mode $TEM_{00}$ and to block light of modes other than $TEM_{00}$. As a result, the emitted beam 310 has an M value of nearly one. When the beam 310 has an M value of one, this beam 310 is most effective for forming incisions as the beam 310 will have a small waist in comparison to its Rayleigh Range. Alternately, the aperture 310 can be selected to block more or less of the available gain cross section. For example, the emitted beam 310 can include light of modes other than $TEM_{00}$ in addition to light of mode $TEM_{00}$. In which case, the beam 310 will have an M value of greater than one. Such a beam can be utilized for ablating tissue or skin, for cauterizing or for coagulation. At an extreme, the aperture 310 can pass all the light 308. As an example, the aperture 312 can be formed by an adjustable iris.

Figure 8A:
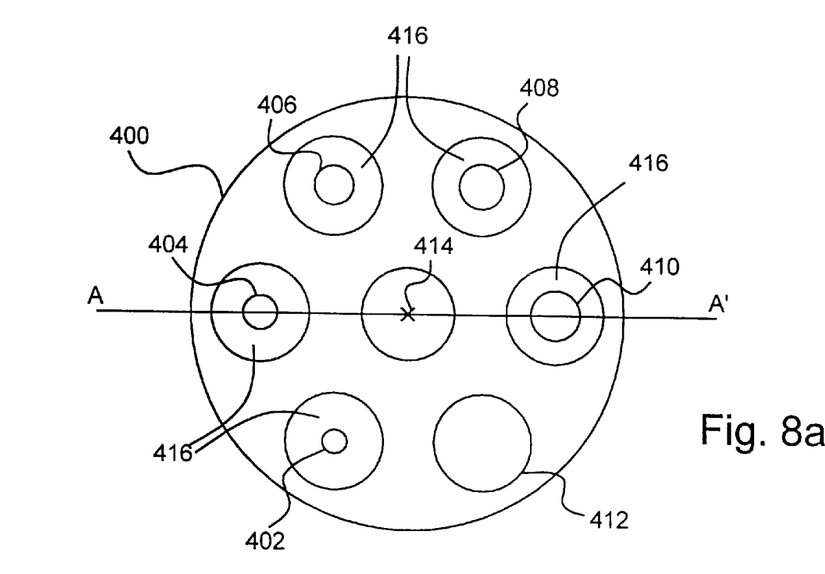
FIGS. 8a–b illustrate a rotatable wheel for achieving the selective aperture in accordance with the present invention.
Figure 8B:
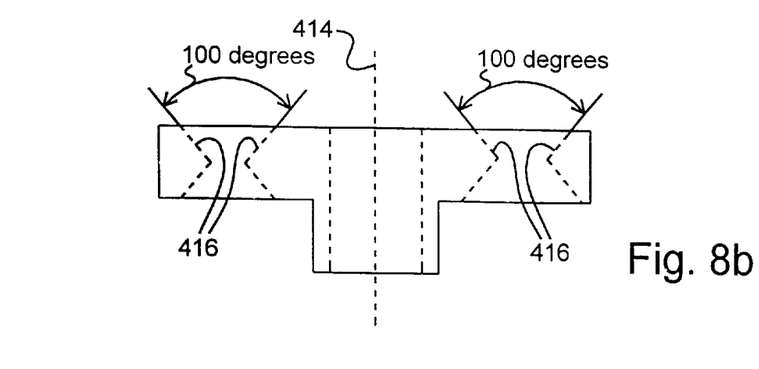

FIG. 8a illustrates a front view of a rotatable wheel 400 for achieving the selective aperture in accordance with the present invention. FIG. 8b illustrates a side sectional view of the rotatable wheel 400 illustrated in FIG. 8a taken at the section line A–A'. The wheel 400 can replace the aperture member 300 illustrated in FIG. 7. In the preferred embodiment, a plurality of apertures 402–412 of progressively larger sizes are formed in the wheel 400. The wheel 400 is rotatable about its center along axis 414 and preferably has a circular outline as seen from the front. It will be apparent, however, that another outline shape can be employed. An important feature of the apertures 402–412 is that each is centered equally distant from the axis 414. As will be explained herein, this feature enables the apertures 402–412 to be exchanged, one for another, by merely rotating the wheel 400 about the axis 414.

Each aperture 402–410 is preferably surrounded by beveled portions 416 of the aperture wheel 400. The beveled portions 416 are preferably cone-shaped having a cone angle of 100 degrees. The beveled portions 416 deflect light out of the beam 308 (FIG. 7). Thus, it will be apparent that the angle formed by each beveled portion 416 need not be 100 degrees. Rather, the angle formed by the beveled portions can be between zero and 90 degrees or between 90 degrees and 180 degrees. This is because if zero, 90 or 180 degrees were to be utilized, light which strikes the area of the wheel 400 surrounding an aperture 402–412 would tend to reflect back into the beam 308. The aperture 412, however, does not require a beveled portion because the aperture 412 is preferably sized to pass all of the beam 308 (FIG. 7). In the preferred embodiment, the aperture wheel 400 is formed of gold-plated aluminum.

FIG. 9 illustrates the rotatable wheel of FIGS. 8a–b in addition to a stepper motor 500 for selecting one of the apertures 402–412 of FIGS. 8a–b in accordance with the present invention. A shaft 502 couples the stepper motor 500 to the aperture wheel 400. In the preferred embodiment, the shaft 502 is flexible (i.e., it can bend, but not twist) so as to avoid mechanical binding which might result due to any misalignment of the axis of rotation of the stepper motor 500 and the axis of rotation 414 (FIGS. 8a–b) of the wheel 400. The stepper motor 500 is controlled by the stepper motor controller 222 (FIG. 6) under control of the CPU 200 (FIG. 6). In response to a command from the CPU 200 for a change in aperture, the stepper motor 500 rotates the shaft 502 and aperture wheel 400 such that a selected one of the apertures 402–412 (FIGS. 8a–b) is aligned with the longitudinal axis of the crystal 302.

In the preferred embodiment, each laser 104, 108 is provided a selectively adjustable aperture. For example, each laser 104, 108 is equipped with a corresponding stepper-motor 500 and aperture wheel 400. Such an arrangement provides exceptional versatility and control over the beam 114 emitted from the scanner handpiece 132. For example, the laser 104 can be configured for a small waist size for forming an incision, while the laser 108 can be configured for a larger waist size for cauterizing the incision. By switching back and forth between pulses from each of the two lasers 104, 108, an incision can be cauterized concurrently as it is being made. Alternately, one of the lasers 104 can be configured for ablating skin while the other laser 108 is configured for performing coagulation or one laser could be configured for large area ablation while another is optimized for fine ablation or coagulation.

According to an alternate embodiment of the present invention, the system includes a single laser source, such as the laser 104 or 108, that is equipped with a selectively adjustable aperture. The selected aperture can be rapidly changed during the performance of a procedure (i.e. "on-the-fly"). For example, by rapidly switching between forming an incision and cauterizing as the laser beam is pulsed, the laser system can cauterize an incision while it is being made. Although the functions are performed successively, by rapidly switching back and forth between appropriate apertures (time-division-multiplexing) in relation to the speed at which the incision is being made, the functions are effectively performed concurrently.

In accordance with yet another aspect of the invention, a degree of misalignment between the selected one of the apertures 402–412 (FIGS. 8a–b) and the longitudinal axis of the crystal 302 (FIG. 7) tends to deflect the beam 114 (FIG. 5) as it exits the handpiece 132 (FIG. 5). The amount of deflection of the beam 114 is related to the amount of misalignment between the aperture 402–412 and the axis of the crystal 302. Accordingly, the beam 114 can be appropriately directed to the surface 134 (FIG. 5) or scanned over an area of the surface 134 (FIG. 5) by rotating the wheel 400 in increments smaller than the amount of rotation required to change to a different one of the apertures 402–412.

The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A pulsed laser delivery apparatus comprising:
   a. a first material capable of lasing;
   b. a first pair of reflective surfaces oriented substantially parallel to one another for reflecting light emitted from the first material therebetween thereby forming a first laser beam;
   c. a member having a substantially circular aperture wherein the member is positioned between the first pair of reflective surfaces wherein the aperture passes the first laser beam and wherein the size of the aperture is selectively adjustable; and
   d. means for alternately selecting between aperture sizes within the member to optimize the first laser beam with respect to tissue interaction characteristics of the first laser beam.

2. The laser delivery apparatus according to claim 1 further comprising an articulated arm and one or more refocussing optics for refocussing the laser beam as it travels through the arm.

3. The laser delivery apparatus according to claim 1 wherein the first material includes erbium.

4. The pulsed laser delivery apparatus according to claim 1 wherein the first laser beam is selectively optimized for one or more of a group including ablation, cutting and coagulation.

5. The laser delivery apparatus according to claim 1 wherein the aperture is surrounded by a beveled portion of the member.

6. The laser delivery apparatus according to claim 5 wherein the beveled portion is cone shaped having a cone angle of at least 100 degrees.

7. A laser delivery apparatus comprising:
   a. a first material capable of lasing;
   b. a first pair of reflective surfaces oriented substantially parallel to one another for reflecting light emitted from the first material therebetween thereby forming a first laser beam;
   c. a member having a substantially circular aperture wherein the member is positioned between the first pair of reflective surfaces wherein the aperture passes the first laser beam and wherein the size of the aperture is selectively adjustable for modulating modes of the first laser beam to optimize the first laser beam with respect to tissue interaction characteristics of the first laser beam;
   d. a second material capable of lasing;
   e. a second pair of reflective surfaces oriented substantially parallel to one another for reflecting light emitted from the second material therebetween thereby forming a second laser beam; and f. means for directing the first laser beam and the second laser beam to a surface to be treated.

8. The laser delivery apparatus according to claim 7 further comprising means for selecting a different aperture size for the first and second laser beams such that two functions can be concurrently performed in successive alternating pulses.

9. The laser delivery apparatus according to claim 7 further comprising an articulated arm and one or more refocussing optics for refocussing the laser beam as it travels through the arm.

10. The laser delivery apparatus according to claim 7 wherein the first material includes erbium.

11. The laser delivery apparatus according to claim 7 wherein the first laser beam is selectively optimized for one or more of a group including ablation, cutting and coagulation.

12. The laser delivery apparatus according to claim 7 wherein the aperture is surrounded by a beveled portion of the member.

13. The laser delivery apparatus according to claim 12 wherein the beveled portion is cone shaped having a cone angle of at least 100 degrees.

14. A pulsed laser delivery apparatus comprising:

a. a laser crystal having a longitudinal axis;

b. a pair of reflective surfaces oriented substantially parallel to one another for reflecting light emitted from the laser crystal therebetween thereby forming a laser beam;

c. a rotatable member positioned between the pair of reflective surfaces and having an axis of rotation and a plurality of apertures wherein the axis of rotation is parallel to the longitudinal axis of the laser crystal and wherein at least one aperture is larger than another; and d. a control member coupled to the rotatable member to select between aperture sizes within the rotatable member to optimize the first laser beam with respect to tissue interaction characteristics of the first laser beam.

15. The laser delivery apparatus according to claim 14 further comprising an articulated arm and one or more refocussing optics for refocussing the laser beam as the laser beam travels through the arm.

16. The laser delivery apparatus according to claim 14 wherein the laser crystal includes erbium.

17. The pulsed laser delivery according to claim 14 wherein the first laser beam is selectively optimized for one or more of a group including ablation, cutting and coagulation.

18. The laser delivery apparatus according to claim 14 wherein at least one of the plurality of apertures is surrounded by a beveled portion of the rotatable member.

19. The laser delivery apparatus according to claim 18 wherein the beveled portion is cone shaped having a cone angle of at least 100 degrees.

20. An adjustable laser delivery apparatus, configured to optimize delivery of a laser beam with respect to tissue interaction characteristics of the laser beam, the apparatus comprising:

a. a first laser crystal having a first longitudinal axis;

b. a first pair of reflective surfaces oriented substantially parallel to one another for reflecting light emitted from the first laser crystal therebetween thereby forming a first laser beam;

c. a first rotatable member positioned between the first pair of reflective surfaces and having a first axis of rotation and a first plurality of apertures wherein the first axis of rotation is parallel to the first longitudinal axis of the first laser crystal and wherein a selected one of the first plurality of apertures is positioned to pass the first laser beam;

d. a second laser crystal having a second longitudinal axis;

e. a second pair of reflective surfaces oriented substantially parallel to one another for reflecting light emitted from the second laser crystal therebetween thereby forming a second laser beam;

f. a second rotatable member having a second axis of rotation and a second plurality of apertures wherein the second axis of rotation is parallel to the second longitudinal axis of the second laser crystal and wherein a selected one of the second plurality of apertures is positioned to pass the second laser beam; and g. an optical system for directing the first laser beam and the second laser beam to a surface to be treated.

21. The laser delivery apparatus according to claim 20 wherein the optical system includes an articulated arm and one or more refocussing optics for refocussing the first laser beam and the second laser beam.

22. The laser delivery apparatus according to claim 20 wherein the first laser crystal includes erbium.

23. The adjustable laser delivery apparatus according to claim 20 wherein the laser beam is selectively optimized for one or more of a group including ablation, cutting and coagulation.

24. The laser delivery apparatus according to claim 20 wherein at least one of the first plurality of apertures is surrounded by a beveled portion of the first rotatable member.

25. The laser delivery apparatus according to claim 24 wherein the beveled portion is cone shaped having a cone angle of at least 100 degrees.

26. A laser delivery apparatus comprising:

a. a first laser crystal having a longitudinal axis;

b. a first pair of reflective surfaces oriented substantially parallel to one another for reflecting light emitted from the first laser crystal therebetween thereby forming a first laser beam;

c. a rotatable member positioned between the first pair of reflective surfaces and having an axis of rotation and a plurality of apertures wherein the axis of rotation is parallel to the longitudinal axis of the first laser crystal and wherein a selected one of the plurality of apertures is positioned to pass the first laser beam;

d. a second laser crystal having a longitudinal axis;

e. a second pair of reflective surfaces oriented substantially parallel to one another for reflecting light emitted from the second laser crystal therebetween thereby forming a second laser beam; and f. means for directing the first laser beam and the second laser beam to a surface to optimize the first laser beam and the second laser beam with respect to tissue interaction characteristics of the first laser beam and the second laser beam.

27. The laser delivery apparatus according to claim 26 wherein at least one of the plurality of apertures is surrounded by a beveled portion of the rotatable member.

28. The laser delivery apparatus according to claim 27 wherein the beveled portion is cone shaped having a cone angle of at least 100 degrees.

29. The laser delivery apparatus according to claim 26 further comprising an articulated arm and one or more refocussing optics for refocussing the first and second laser beams as they travel through the arm.

30. The laser delivery apparatus according to claim 26 wherein at least one of the first and second laser crystal includes erbium.

31. The laser delivery apparatus according to claim 26 wherein the first laser beam and the second laser beam are selectively optimized for one or more of a group including ablation, cutting and coagulation.

32. A method of delivering laser pulses comprising the steps of:
  a. generating a first set of one or more pulses from a first laser source comprising a first laser medium and a pair of laser mirrors for reflecting laser light through the first laser medium and including a first aperture member having a first aperture positioned between the pair of laser mirrors through which the first set of pulses pass; and
  b. generating a second set of one or more pulses from a second laser source comprising a second laser medium and a second pair of laser mirrors for reflecting laser light through the second laser medium and including a second aperture member positioned between the second pair of laser mirrors having a second aperture through which the second set of pulses pass.

33. The method of claim 32, wherein the first aperture member comprises a plurality of apertures and wherein the first aperture is selected from the plurality of apertures.

34. The method of claim 33, wherein the aperture member is rotatable and wherein the first aperture is selected from the plurality of apertures by rotating the aperture member between the first laser medium and the first laser mirror.

35. The method of claim 32, further comprising combining the first set of pulses and the second set of pulses into a single laser output.

36. The method of claim 35, further comprising directing the single laser output to a treatment surface through an articulated arm, wherein the articulated arm comprises a plurality of lenses.

* * * * *